United States Patent [19]

Kempe et al.

[11] Patent Number: 4,672,128
[45] Date of Patent: Jun. 9, 1987

[54] PREPARATION OF IMIDAZOLE-4(5)-MONOCARBOXYLIC ACIDS AND THEIR SALTS OR BETAINES

[75] Inventors: Uwe Kempe, Dannstadt-Schauernheim; Toni Dockner, Meckenheim; Rolf Schlick, Ludwigshafen, all of Fed. Rep. of Germany

[73] Assignee: BASF Aktiengesellschaft, Ludwigshafen, Fed. Rep. of Germany

[21] Appl. No.: 758,303

[22] Filed: Jul. 24, 1985

[30] Foreign Application Priority Data

Jul. 24, 1984 [DE] Fed. Rep. of Germany ..... 34271368

[51] Int. Cl.$^4$ ............................................. C07D 233/90
[52] U.S. Cl. ................................................. 548/343
[58] Field of Search ....................................... 548/343

[56] References Cited

U.S. PATENT DOCUMENTS 3,023,210 2/1962 Schutt ........................... 548/343 X

OTHER PUBLICATIONS

F. L. Pymann, *J. Chem. Soc.*, 109 (1916), 186–202.
W. Hubball and F. L. Pymann, *J. Chem. Soc.*, 131 (1928), 21–32.
R. Weidenhagen and H. Wegner, *Ber.* 70 (1937), 2309.
R. G. Fargher and F. L. Pymann, *J. Chem. Soc.*, 115 (1919), 217.
CA 90: 72,189z (1979).
CA 98: 179,384b (1983).

*Primary Examiner*—Richard A. Schwartz
*Attorney, Agent, or Firm*—John H. Shurtleff

[57] ABSTRACT

Imidazole-4(5)-monocarboxylic acids and their salts or betaines are prepared by reacting an imidazole with carbon dioxide and an alkali metal carbonate, an alkali metal bicarbonate and/or an alkali metal hydroxide at from 140° to 230° C. and under from 2 to 350 bar and, if desired, then reacting the product with an acid.

The imidazole-4(5)-monocarboxylic acids which can be prepared by the process of the invention are useful starting materials for the preparation of dyes, crop protection agents and drugs.

11 Claims, No Drawings

PREPARATION OF IMIDAZOLE-4(5)-MONOCARBOXYLIC ACIDS AND THEIR SALTS OR BETAINES

The present invention relates to a novel process for the preparation of imidazole-4(5)-monocarboxylic acids and their salts or betaines by reacting an imidazole with carbon dioxide and an alkali metal carbonate, an alkali metal bicarbonate and/or an alkali metal hydroxide at from 140° to 230° C. under from 2 to 350 bar and, if desired, then reacting the product with an acid.

(2 synthesis routes have become important in practice for the preparation of imidazole-4(5)-monocarboxylic acids: (1) the oxidation of 4-hydroxymethylimidazoles with nitric acid (F. L. Pymann, J. Chem. Soc. 109 (1916), 186–202, W. Hubball and F. L. Pymann, J. Chem. Soc. 131 (1928), 21–32, and R. Weidenhagen and H. Wegner, Ber. 70 (1937), 2309), and (2) the partial decarboxylation of 4,5-imidazoledicarboxylic acids or 2-substituted 4,5-imidazoledicarboxylic acids in boiling aniline (R. G. Fargher and F. L. Pymann, J. Chem. Soc. 115 (1919), 217), with subsequent hydrolysis of the resulting 4-imidazolecarboxanilides by heating in acids or alkalis (CA 90: 72 189 z). Another route to imidazole-4-carboxylic acids is opened up by the oxidative desulfurization of 2-mercaptoimidazole-4-carboxylic acid derivatives (Weidenhagen, loc. cit., page 2310) and the oxidation of the corresponding imidazoledithiocarboxylic acids with a hydroperoxide (CA 98: 17 93 84 b (1983)). All these processes have in common the fact that they are difficult to carry out industrially on a large scale or start from expensive intermediate stages which are difficult to implement industrially on a large scale.

German Published Application DAS NO. 1,033,667 describes a process for the preparation of heterocyclic carboxylic acids by reacting an aromatic heterocycle with carbon dioxide in the presence of an alkali metal carbonate under superatmospheric pressure. Although the temperature range is stated as being above 150° C. (column 1, line 8), it is pointed out that various products are formed from the same starting materials at different reaction temperatures. For example, under otherwise identical conditions, pyrazole (column 1, lines 15 to 50) gives the salt of the 3,5-dicarboxylic acid at 230° C., and the salt of the 4-monocarboxylic acid at a higher temperature, i.e. 270° C. In the case of the reaction of imidazole and its derivatives (Examples 1, 2, 5, 6, 11, 12 and 15), the temperature employed is in each case from 250° to 280° C.; the end products obtained in each case are salts of the corresponding imidazole-4,5-dicarboxylic acids. The best yields of imidazoledicarboxylic acids are obtained at 260° C. and with the use of catalysts, i.e. cadmium fluoride (Example 1). As shown in the Examples, imidazolemonocarboxylic acids are not formed in substantial amounts. Monocarboxylic acids are obtained, as shown in the published application, in the case of unstable free dicarboxylic acids, e.g. 1,2,4-triazoledicarboxylic acids, with elimination of $CO_2$ (column 2, lines 20 to 23). The Examples show that, for other heterocycles, monocarboxylic acids are formed only under certain conditions, for example at elevated temperatures (260° C.) and for a particular structure, as in the case of indazoles (Example 13). In the case of triazole and its 3-monocarboxylic acid, the dicarboxylic acid is obtained at 220° C. (Example 17) and higher temperatures, e.g. from 260° to 270° C. (Examples 9, 16 and 19); further treatment with concentrated hydrochloric acid at elevated temperatures is required in order to obtain a reaction product containing significant amounts of monocarboxylic acids or dicarboxylic acid. As the Examples and description show, the yields in the reaction and in particular the purity of the end product are advantageously affected by catalysts (column 3, lines 22 to 37).

We have found that imidazole-4(5)-monocarboxylic acids of the formula

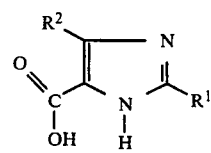

where $R^1$ and $R^2$ are identical or different and are each hydrogen or an aliphatic, araliphatic, aromatic or cycloaliphatic radical, or their salts or betaines are advantageously obtained by reacting an imidazole with carbon dioxide and an alkali metal compound at elevated temperatures and under superatmospheric pressure if an imidazole of the formula

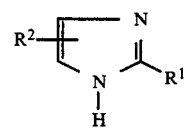

where $R^1$ and $R^2$ have the above meanings, is reacted with carbon dioxide and an alkali metal carbonate, an alkali metal bicarbonate and/or an alkali metal hydroxide at from 140° to 230° C. and under from 2 to 350 bar and, if desired, the product is then reacted with an acid.

Where potassium carbonate and 2,4-dimethylimidazole are used, the reaction can be represented by the following equation:

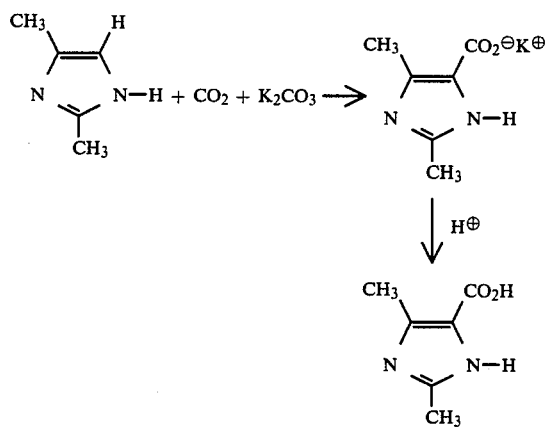

Compared with the conventional process, the process according to the invention gives imidazole-4(5)-monocarboxylic acids and their salts and betaines in better yield and purity and by a simpler and more economical route. In view of the prior art, all these advantageous results are surprising. On the basis of German Published Application DAS 1,033,667, it was to be expected that the lower temperature according to the invention, of no more than 220° C., would result only in the formation of the corresponding dicarboxylic acid compounds, without significant amounts of monocarboxylic acid. It was also surprising that the end product was obtained in pure form and in high yield although the reactions take place in the absence of the metal catalysts described in the published application. Moreover, it is surprising that, for the preparation of the monocarboxylic acids, treatment with concentrated hydrochloric acid at elevated temperatures can be dispensed with in most cases.

The reaction of starting material II with carbon dioxide can be carried out using stoichiometric amounts or an excess of one or other of the components. Advantageously, from 2 to 100, preferably from 5 to 30, moles of carbon dioxide are employed per mole of starting material II. Carbon dioxide can be added in solid or gaseous form, but is advantageously used in liquid form.

Alkali metal compounds used are alkali metal hydroxides, alkali metal bicarbonates or, preferably, alkali metal carbonates or mixtures of these. The potassium compounds are preferred, examples of suitable compounds being potassium hydroxide, potassium bicarbonate and preferably potassium carbonate. The alkali metal compounds according to the invention are reacted with the starting material II in a stoichiometric amount or using an excess of one or other of the components. Advantageously, from 1 to 4, preferably from 1 to 2.5, moles of alkali metal compound are employed per mole of starting material II.

Preferred starting materials II, and accordingly preferred end products I, are those of the formulae where $R^1$ and $R^2$ are identical or different and are each hydrogen, alkyl or alkyl of 1 to 18, preferably 1 to 8, in particular 1 to 4, carbon atoms which is substituted by alkoxy groups, in particular 1- and 2-alkoxy groups, each of which is advantageously of 1 to 8, preferably 1 to 4, carbon atoms, or $R^1$ and $R^2$ are each aralkyl or alkylaryl of 7 to 12 carbon atoms, cycloalkyl of 5 to 8 carbon atoms or an aromatic radical, e.g. phenyl or naphthyl. The abovementioned radicals may be further substituted by groups which are inert under the reaction conditions, e.g. alkyl or alkoxy groups of 1 to 4 carbon atoms.

Examples of imidazoles which are suitable as starting materials II are methyl-, ethyl-, propyl-, isopropyl-, benzyl-, phenyl-, butyl-, sec.-butyl-, isobutyl-, tert.-butyl- and cyclohexylimidazole and the corresponding 4(5)-imidazoles, 2-methoxy-, 2-ethoxy-, 2-propoxy-, 2-isopropoxy-, 2-butoxy-, 2-isobutoxy-, 2-sec.-butoxy- and 2-tert.-butoxymethylimidazole and the corresponding 2-ethyl-, 2-propyl-, 2-isopropyl-, 2-butyl-, 2-sec.-butyl- and 2-isobutylimidazoles which are substituted in the 1-position of the alkyl chain by methoxy, ethoxy, propoxy, isopropoxy, butoxy, isobutoxy, sec.-butoxy or tert-butoxy, homologous imidazoles substituted in the 4-position of the ring by the abovementioned alkoxyalkyl groups; 2,4-dimethyl-, 2,4-diethyl-, 2,4-dipropyl-, 2,4-diisopropyl-, 2,4-dibutyl-, 2,4-di-sec.-butyl-, 2,4-diisobutyl- and 2,4-di-tert.-butylimidazole; imidazole; 2-phenyl-4-methyl- and 2-ethyl-4-methylimidazole and the corresponding imidazoles substituted in the 2,4-position by different substituents selected from those stated above. Imidazole, 2-methylimidazole, 2-ethyl-, 2-isopropyl-, 2-phenyl-, 2-cyclohexyl- and 2-butylimidazole, 2,4-dimethylimidazole, 2-ethyl-4-methylimidazole, 4-methylimidazole and 2-methoxymethylimidazole are preferred.

The reaction is carried out at from 140° to 230° C., advantageously from 145° to 220° C., preferably from 149° to 220° C., and under from 2 to 350, advantageously from 10 to 180, preferably from 50 to 160, bar, either continuously or batchwise. Although a catalyst may be used, the reaction is as a rule carried out in the absence of a catalyst. The reaction may also be effected in the presence of an organic solvent, e.g. methanol, toluene or dimethylformamide, but is generally effected in the absence of an organic solvent and of water.

The reaction can be carried out as follows: a mixture of starting material II, carbon dioxide and the alkali metal compound is kept at the reaction temperature and under the reaction pressure, expediently for from 1 to 30, advantageously for from 1.5 to 15, hours. Starting material II and the alkali metal compound are advantageously used in finely divided form.

The end product is isolated from the reaction mixture in a conventional manner, for example by comminuting the solid reaction mixture or the solid residue of the mixture, suspending the comminuted product in water and filtering the suspension. In this way, the end product is generally obtained as a water-soluble salt of the 4-carboxylic acid. The free 4-carboxylic acid can be isolated from the reaction mixture by acidification, this being done using any organic or, expediently, inorganic acid, advantageously a mineral acid, preferably hydrochloric acid, sulfuric acid or phosphoric acid. The suspension or solution is preferably acidified to a pH of from 2 to 6.

The end product preferably contains the monocarboxylic acid in the form of its betaine of the formula

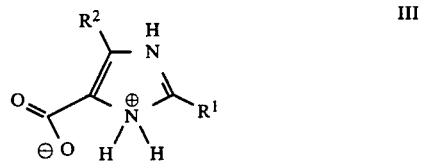

where $R^1$ and $R^2$ have the above general and preferred meanings.

The imidazole-4(5)-monocarboxylic acids which can be prepared by the process of the invention are useful starting materials for the preparation of dyes, crop protection agents and drugs. For example, secondary products of the novel end products I, i.e. the N-substituted monocarboxylates, e.g. the ethyl esters, are anesthetics used in veterinary medicine. Regarding the use of these compounds, reference may be made to the abovementioned publications.

EXAMPLE 1

2,5-Dimethylimidazole-4-carboxylic acid 12 g (0.125 mole) of 2,4-dimethylimidazole, 42.5 g (0.3 mole) of potassium carbonate and 100 ml of liquid carbon dioxide were stirred for 5 hours at 150° C. in an autoclave, the reaction pressure being 130 bar. The reacted mixture was pulverized and suspended in 100 ml of water, and the stirred suspension was brought to pH 5–6 with hydrochloric acid. The precipitate which separated out was filtered off and dried to give 13 g (74% of theory) of pure 2,5-dimethylimidazole-4-carboxylic acid of melting point 234° C. (decomposition).

EXAMPLES 2 TO 8

The reactions in Examples 2 to 8 are carried out similarly to Example 1.

| Example | Starting imidazole II R¹, R² | g | (mole) | Imidazole-4-carboxylic acid I R¹, R² | Amount g | Yield % | Decomposition temperature °C. |
|---|---|---|---|---|---|---|---|
| 2 | 4-methyl- | 16.4 | 0.2 | 5-methyl- | 11.8 | 47 | 222 |
| 3 | 2-methyl- | 16.4 | 0.2 | 2-methyl- | 17.5 | 69 | 258 |
| 4 | 2-ethyl- | 19.2 | 0.2 | 2-ethyl- | 11.8 | 42 | 252 |
| 5 | 2-isopropyl- | 11.0 | 0.1 | 2-isopropyl- | 6.9 | 45 | 253 |
| 6 | 2-phenyl- | 14.4 | 0.1 | 2-phenyl- | 7.5 | 40 | 200 |
| 7 | 2-methoxymethyl- | 5.6 | 0.05 | 2-methoxymethyl- | 3.5 | 44.8 | 220 |
| 8 | 2-benzyl- | 15.8 | 0.1 | 2-benzyl- | 12 | 59 | 243 |

EXAMPLE 9

544 g (8 moles) of imidazole, 1,380 g (10 moles) of potassium carbonate and 1,000 ml of liquid $CO_2$ were reacted for 2.5 hours under 120 bar and at 219° C. in an autoclave. The end product was precipitated by acidifying the mixture to pH 3 and slowly heating it to 100° C. in the course of 1 hour. The product was dried to give 606 g (67.6% of theory) of imidazole-4-carboxylic acid, which melted at 220° C. with decomposition (evolution of $CO_2$).

EXAMPLE 10

The reaction of Example 9 was carried out using 10 moles of potassium hydroxide instead of potassium carbonate. 510 g (58% of theory) of imidazole-4-carboxylic acid of melting point 220° C. were obtained.

We claim:

1. A process for the preparation of an imidazole-4(5)-monocarboxylic acid of the formula

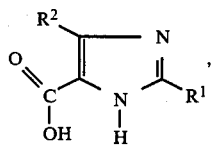

or its salt or betaine, wherein $R^1$ and $R^2$ are identical or different and are each alkyl of 1 to 18 carbon atoms, alkyl of 1 to 18 carbon atoms which is substituted by 1 or 2 alkoxy groups, aralkyl or alkylaryl of 7 to 12 carbon atoms, cycloalkyl of 5 to 8 carbon atoms or an aromatic group, the aralkyl, alkylaryl, cycloalkyl or aromatic groups being unsubstituted or substituted by alkyl or alkoxy groups of 1 to 4 carbon atoms, or wherein one of the groups $R^1$ or $R^2$ is hydrogen, which process comprises:

reacting an imidazole of the formula

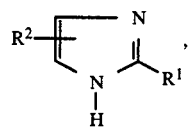

wherein $R^1$ and $R^2$ have the above meanings, with carbon dioxide and an alkali metal compound selected from the group consisting of alkali metal carbonates, alkali metal bicarbonates and alkali metal hydroxides at from 140° to 230° C. and under a pressure from 2 to 180 bar and with the proviso that, if the free 4(5)-monocarboxylic acid I is desired, then reacting the salt of betaine obtained as the initial product with an acid.

2. A process as claimed in claim 1, wherein from 1 to 100 moles of carbon dioxide are used per mole of starting material II.

3. A process as claimed in claim 1, wherein from 1 to 4 moles of an alkali metal compound are used per mole of starting material II.

4. A process for the preparation of imidazole-4-monocarboxylic acid which comprises reacting imidazole with carbon dioxide and an alkali metal compound selected from the group consisting of alkali metal carbonates, alkali metal bicarbonates and alkali metal hydroxides at from 140° to 230° C. and under a pressure from 2 to 180 bar and then acidifying the reaction mixture while heating to form the free monocarboxylic acid.

5. A process as claimed in claim 4 wherein the reaction mixture is acidified to a pH of from 2 to 6 to form the free monocarboxylic acid.

6. A process as claimed in claim 4 wherein from 1 to 100 moles of carbon dioxide are used per mole of the imidazole starting material.

7. A process as claimed in claim 4 wherein from 1 to 4 moles of the alkali metal compound are used per mole of the imidazole starting material.

8. A process as claimed in claim 1 wherein the reaction temperature is 145° to 220° C.

9. A process as claimed in claim 4 wherein the reaction temperature is 145° to 220° C.

10. A process as claimed in claim 1 wherein the reaction pressure is 10 to 180 bar.

11. A process as claimed in claim 4 wherein the reaction pressure is 10 to 180 bar.

* * * * *

UNITED STATES PATENT AND TRADEMARK OFFICE
CERTIFICATE OF CORRECTION

PATENT NO. : 4,672,128
DATED : June 9, 1987
INVENTOR(S) : Uwe Kempe, Toni Dockner, and Rolf Schlick It is certified that error appears in the above-identified patent and that said Letters Patent is hereby corrected as shown below:

Claim 1, next to the last line: change "of" to --or--.

Signed and Sealed this

Fifth Day of April, 1988

*Attest:*

DONALD J. QUIGG

*Attesting Officer*    Commissioner of Patents and Trademarks